United States Patent
Ross (10) Patent No.: US 7,399,278 B1
(45) Date of Patent: Jul. 15, 2008

(54) METHOD AND SYSTEM FOR MEASURING AMNIOTIC FLUID VOLUME AND/OR ASSESSING FETAL WEIGHT

(75) Inventor: Michael G. Ross, Los Angeles, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 10/836,963

(22) Filed: Apr. 30, 2004

Related U.S. Application Data (60) Provisional application No. 60/467,983, filed on May 5, 2003.

(51) Int. Cl.
A61B 8/00 (2006.01)
G06K 9/00 (2006.01)

(52) U.S. Cl. ........................................ 600/437; 382/128
(58) Field of Classification Search ................. 382/173, 382/181, 254; 600/437
See application file for complete search history.

(56) References Cited

U.S. PATENT DOCUMENTS

| | | | |
|---|---|---|---|
| 4,233,032 A | 11/1980 | Statland et al. |
| 4,257,278 A | 3/1981 | Papadofrangakis et al. |
| 4,547,464 A | 10/1985 | Socol |
| 4,722,730 A | 2/1988 | Levy et al. |
| 5,235,985 A | 8/1993 | McMorrow et al. |
| 5,370,135 A | 12/1994 | Dullien |
| 5,405,751 A | 4/1995 | Roncarolo |
| 5,494,044 A | 2/1996 | Sundberg |
| 5,512,281 A | 4/1996 | Ruprecht |
| 5,588,435 A | 12/1996 | Weng et al. |
| 5,592,941 A | 1/1997 | McMorrow |
| 5,605,155 A | 2/1997 | Chalana et al. |
| 5,612,028 A | 3/1997 | Sackier et al. |
| 5,644,513 A | 7/1997 | Rudin et al. |
| 5,782,767 A | 7/1998 | Pretlow, III |
| 5,783,396 A | 7/1998 | Voroteliak et al. |
| 5,860,929 A | 1/1999 | Rubin et al. |

(Continued)

FOREIGN PATENT DOCUMENTS

EP 0471721 4/1995

(Continued)

OTHER PUBLICATIONS

Sagiv, C. et al "Application of a Semiautomatic Boundary Detection Algorithm for Assessment of Amniotic Fluid Quantity"□□Ultrasound in Medicine & Biology, vol. 25, No. 4, May 1999. pp. 515-526 (Abstract).*

(Continued)

Primary Examiner—Eric F. Winakur
Assistant Examiner—Michael Rozanski
(74) Attorney, Agent, or Firm—Blakely Sokoloff Taylor & Zafman LLP (57) ABSTRACT

A system is described for measuring amniotic fluid volume and/or assessing fetal weight. The system includes an ultrasound apparatus to scan a pregnant uterus and to generate data representative of a three-dimensional construction of the scanned uterus, and a processor to compute a volume of amniotic fluid or weight of fetal tissue based on the three-dimensional construction of the scanned uterus. Also a method of computing a volume of amniotic fluid and/or a weight of fetal tissue.

26 Claims, 3 Drawing Sheets

U.S. PATENT DOCUMENTS

| | | | |
|---|---|---|---|
| 5,879,937 | A | 3/1999 | Roncarolo |
| 5,899,861 | A | 5/1999 | Friemel et al. |
| 6,102,861 | A | 8/2000 | Avila et al. |
| 6,110,111 | A | 8/2000 | Barnard |
| 6,213,949 | B1 | 4/2001 | Ganguly et al. |
| 6,276,211 | B1 | 8/2001 | Smith |
| 6,306,089 | B1 * | 10/2001 | Coleman et al. ............ 600/437 |
| 6,346,124 | B1 | 2/2002 | Geiser et al. |
| 6,359,190 | B1 | 3/2002 | Ter-Ovanesyan et al. |
| 6,375,616 | B1 | 4/2002 | Soferman et al. |
| 6,390,984 | B1 | 5/2002 | Pan et al. |
| 6,399,585 | B1 | 6/2002 | Larson et al. |
| 6,406,431 | B1 | 6/2002 | Barnard et al. |
| 6,535,835 | B1 | 3/2003 | Rubin et al. |
| 6,544,175 | B1 | 4/2003 | Newman |
| 6,544,178 | B1 | 4/2003 | Grenon et al. |
| 6,569,097 | B1 | 5/2003 | McMorrow et al. |
| 6,575,907 | B1 * | 6/2003 | Soferman et al. ........... 600/438 |
| 6,676,605 | B2 | 1/2004 | Barnard et al. |
| 6,692,441 | B1 | 2/2004 | Poland et al. |
| 6,695,780 | B1 | 2/2004 | Nahum et al. |
| 6,716,174 | B1 | 4/2004 | Li |
| 6,740,036 | B1 | 5/2004 | Lee et al. |
| 2002/0007680 | A1 | 1/2002 | Wiesauer |
| 2002/0133075 | A1 * | 9/2002 | Abdelhak .................... 600/443 |
| 2004/0024302 | A1 * | 2/2004 | Chalana et al. ............. 600/407 |

FOREIGN PATENT DOCUMENTS

| | | |
|---|---|---|
| WO | WO 90/13261 | 11/1990 |
| WO | WO 99/61598 | 12/1999 |
| WO | WO-2004/017834 | 7/2003 |
| WO | WO 2004/001284 | 2/2004 |
| WO | WO-2004/041094 | 5/2004 |

OTHER PUBLICATIONS

Grover, J. et al "Three-Dimensional Method for Determination of Amniotic Fluid Volume in Intrauterine Pockets", Obstetriucs & Gynecology 1997:909:pp. 1007-1010.*

Albuquerque CA, et al.: Relation between oligohydramnios and spinal flexion in the human fetus. Early Hum. Dev. (2002) 68:119-126.

Antsaklis, AJ, et al.: Prenatal diagnosis of fetal primary cytomegalovirus infection. BJOG (2000) 107:84-88.

Awad, MM: The fetal biophysical profile score: a routine screening technique for pregnant women. J Egypt Soc Obstet Gynecol, Abstract (1991) 17:27-32.

Benacerraf, BR, et al.: Sonographic Observation of Amniotic Rupture without amniotic band syndrome. J Ultrasound Med (1992) 11:109-111.

Bianco, A, et al.: Measurement of the amniotic fluid index with and without color doppler, J Perinat Med (1999) 27:245-249.

Biggio, JR, et al.: Hydramnios prediction of adverse perinatal outcome. Obstet Gynecol (1999) 94(5 pt 1):773-777.

Birnholz, JC, et al.: Amniotic fluid accumulation in the first trimester. J Ultrasound Med. (1995) 14(8):597-602.

Blackwell, SC, et al.: Abnormal amniotic fluid volume as a screening test prior to targeted ultrasound. Med Sci Monit (2003) 9(11):MT119-MT122.

Bukowski, R, et al.: Measurement of the deepest vertical pocket (DVP) of amniotic fluid using gray-scale versus color doppler ultrasound. Abstract, American Journal of Obstetrics and Gynecology (2001) 184(1):S105.

Cheng, XY, et al.: Boundary extraction method for three dimensional ultrasonic echo imaging using fuzzy reasoning and relaxation techniques. IEEE Nucl Sci Symp & Med Imaging Conf. (1994) pt. 3:1610-1614.

Claussen, U, et al.: Six years' experience with rappid karyotyping in prenatal diagnosis: correlations between phenotype deleted by ultrasound and fetal karyotype. Prenatal Diagn. (1994) 14(2):113-121.

Conroy, JM, et al.: Hidden markov models for chromosome identification. Proceedings 14th IEEE Symposium on Computer-Based Med Systems (2001) 473-477.

Cosmi, E, et al.: Therapy or prevention of fetal infection by cytomegalovirus with immunoglobulin infusion in pregnant women with primary infection. Acta Biomed Ateneo Parmense (2000) 71(Suppl 1):547-551.

Couvreur, J: Congenital toxoplasmosis: the changing situation over the last 40 years. La Presse Medicale (1999) 28(14):753-757.

Daffos, F, et al.: Prenatal management of 746 pregnancies at risk for congenital toxoplasmosis. New Engl. J. Med. (1988) 318(5):271-279.

Dashe, JS, et al.: Hydramnios: anomaly prevalence and sonographic detection. Obstet Gynecol (2002) 100(1):134-139.

De Keersmaecker, B, et al.: Prenatal diagnosis of brain abnormalities in wolf-hirschhorn (4p-) syndrome. Prenat Diagn. (2002) 22:366-370.

De Spirlet, M, et al.: Isolated antenatal pyelic dilatation: postnatal follow-up and care for vesicoureteral reflux. J Gynecol Obstet Biol Reprod. (Paris). (2002) 31(Suppl 1):2S56-2S63.

DiPietro, JA, et al.: Fetal movement detection: Comparison of the Toitu actograph with ultrasound from 20 weeks gestation. J Matern Fetal Med (1999), 237-242.

Drbohlav, P, et al.: Perinatal outcome of twin pregnancies after fertilization in vitro and after spontaneous conception. Ceska Gynekol (2000) 65(Suppl 1):24-29.

Duck, FA: Nonlinear acoustics in diagnostic ultrasound. Ultrasound Med. Biol. (2002) 28(1):1-18.

Duncomb, GJ, et al.: The effects of overcoming experimental bladder outflow obstruction in fetal sheep. J Matern Fetal Neonatal Med. (2002) 11:130-137.

Eils, R, et al.: Application of confocal laser microscopy and three-dimensional voronoi diagrams for volume and surface estimates of interphase chromosomes. Journal of Microscopy (1995) 177(2):150-161.

Evans, ML, et al.: Fetal cell testing: Societal and ethical speculations. Ann. N.Y. Acad. Sci. (1994) 731:257-261.

Farina, A, et al.: Amniotic fluid volume and onset of labor in physiological pregnancy. American Journal of Perinatology (1999) 16(5):217-221.

Farran, I, et al.: Early amniocentesis with the filtration technique: neonatal outcome in 123 singleton pregnancies. Prenat Diagn. (2002) 22:859-863.

Favre, R, et al.: Early fetal megacystis between 11 and 15 weeks of gestation. Ultrasound Obstet Gynecol (1999) 14:402-406.

Fenton, BW, et al.: Magnetic resonance spectroscopy to detect lecithin in amniotic fluid and fetal lung. Obstet Gynecol (2000) 95(3):457-460.

Fernandez-Moya, JM, et al.: Sonographic, cytogenetic and DNA analysis in four 69,XXX fetuses dianosed in the second trimester. Fetal Diagn Ther (2000) 15:97-101.

Goldkrand, JW, et al.: Comparison of the amniotic fluid index with gray-scale and color doppler ultrasound. J Maternal-Fetal Neonatal Med (2003) 13:318-322.

Goldkrand, JW, et al.: Volumetric umbilical artery blood flow: comparison of the normal versus the single umbilical artery cord. J Matern Fetal Med (2001) 10:116-121.

Gordon, MC, et al.: Complications of third-trimester amniocentesis using continuous ultrasound guidance. Obster Gynecol. (2002) 99(2):255-259.

Gramellini, D, et al.: Amnioinfusion: techniques, indications, and controlled retrospective study of 55 cases. Acta Biomed Ateneo Parmense (2000) 71(Suppl 1):325-329.

Gramellini, D, et al.: Sonographic assessment of amniotic fluid volume between 11 and 24 weeks of gestation: construction of reference intervals related to gestational age. Ultrasound Obstet Gynecol (2001) 17:410-415.

Gratacos, E, et al.: Transient hydropic signs in the donor fetus after fetoscopic laser coagulation in severe twin-twin transfusion syndrome: incidence and clinical relevance. Ultrasound Obstet Gynecol (2002) 19:449-453.

Grover, J, et al.: Three-dimensional method for determination of amniotic fluid volume in intrauterine pockets. Obstet & Gynecol (1997) 90(6):1007-1010.

Han, SJ, et al.: The development of fetal surgery. Yonsei Med. J (2001) 42(6):602-608.

Hansen, WF, et al.: Ureterocele causing anhydramnios successfully treated with percutaneous decompression. Obstet Gynecol (2002) 99(5 pt. 2):953-956.

Hecher, K, et al.: Monitoring of fetuses with intrauterine growth restriction: a longitudinal study. Ultrasound Obstet Gynecol (2001) 18:564-570.

Hellemans, P, et al.: Preliminary results with the use of the ROM-check immunoassay in the early detection of rupture of the amniotic membranes. Euro J of Obs & Gyne and Reprod Biology (1992) 43:173-179.

Herndon, CD, et al.: Consensus on the prenatal management of antenatally detected urological abnormalities. J Urol (2000) 164:1052-1056.

Hielscher, AH, et al.: Near infrared optical tomographic imaging of fluid containing tissues. IEEE International Symposium on Biomedical Imaging (2002) 70-73.

Hill, LM, et al.: Effects of indomethacin on individual amniotic fluid indices in multiple gestations. J Ultrasound Med. (1996) 15(5):395-399.

Hogge, WA, et al.: Prenatal diagnosis of cytomegalovirus (CMV) infection: a preliminary report. Prenatal Diagn. (1993) 13(2):131-136.

Holden, DP, et al.: Lung development in diamniotic twins discordant for complete urinary tract obstruction. Fetal Design Ther (1999) 14:296-300.

Holzbeierlein, J, et al.: The urodynamic profile of myelodysplasia in childhood with spinal closure during gestation. J Urol (2000) 164:1336-1339.

Hombo, Y., et al.: Direct prediction of amniotic fluid volume in the third trimester by 3-dimensional measurements of intrauterine pockets: a tool for routine clinical use. American Journal of Obstetrics and Gynecology (2002) 186:245-250.

Laudy, JA, et al.: Prenatal prediction of pulmonary hypoplasia: clinical, biometric, and doppler velocity correlates. Pediatrics (2002) 109:250-258.

Lerner, B, et al.: Automatic signal classification in fluorescence in situ hybridization images. Cytometry (2001) 43:87-93.

Levine, D, et al.: Fetal thoracic abnormalities: MR Imaging. Radiology (2003) 228:379-388.

Levine, D, et al.: Potential heating effect in the gravid uterus during MR HASTE imaging. J Magn Reson Imaging (2001) 13:856-861.

Levine, D, et al.: Technical factors influencing sonographic visualization of fetal echogenic intracardiac foci. J Clin Ultrasound (2000) 28:479-484.

Liesnard, C, et al.: Prenatal diagnosis of congenital cytomegalovirus infection: prospective study of 237 pregnancies at risk. Obstet Gynecol (2000) 95(6 pt 1):881-888.

Lipitz, S, et al.: Outcome of pregnancies with vertical transmission of primary cytomegalovirus infection. Obstet Gynecol (2002) 100:428-433.

Luo, X, et al.: Analysis of 196 cases of trial of labor with borderline oligohydramnios. Zhonghuz Fu Chan Ke Za Zhi (1998) 33(10):585-587.

Luo, Y, et al.: Clinical application of ultrasonographic indexes for assessment of amniotic fluid volume. Chinese J Obstet Gynecol, Abstract (2001) 36(9):520-522.

Ma, YY, et al.: Study on prenatal diagnosis using fluorescence quantitative polymerase chain reaction for congenital toxoplasmosis. Chinese J Obstet Gynecol, Abstract (2003) 38(1):8-10.

Macedonia, C, et al.: Power doppler imaging of the fetal upper aerodigestive tract using a 4-point standardized evaluation: preliminary report. J Ultrasound Med. (2002) 21:869-878.

Magann, EF, et al.: Amniotic fluid index and single deepest pocket: weak indicators of abnormal amniotic volumes. Obstet Gynecol (2000) 96(5 pt 1):737-740.

Magann, EF, et al.: Amniotic fluid volume assessment in singleton and twin pregnancies. Obstet Gynecol Clin North Am (1999) 26(4):579-593.

Magann, EF, et al.: Amniotic fluid volume estimation and the biophysical profile: a confusion of criteria. Ostet Gynecol (2000) 96(4):640-642.

Magann, EF, et al.: Antenatal testing among 1001 patients at high risk: the role of ultrasonographic estimate of amniotic fluid volume. American Journal of Obstetrics and Gynecology (1999) 180:1330-1336.

Magann, EF, et al.: Comparability of the amniotic fluid index and single deepest pocket measurements in clinical practice. Australian & New Zealand J Obstet Gynaecol (2003) 43:75-77.

Magann, EF, et al.: Determination of amniotic fluid volume in twin pregnancies: ultrasonographic evaluation versus operator estimation. American Journal of Obstetrics and Gynecology (2000) 182(6):1606-1609.

Magann, EF, et al.: How well do the amniotic fluid indexs and single deepest pocket indices (below the 3rd and 5th and above the 95th and 97th percentiles) predict oligohydramnios and hydramnios? American Journal of Obstetrics and Gynecology (2004) 190:164-169.

Magann, EF, et al.: Is amniotic fluid volume status predictive of fetal acidosis at delivery? Australian & New Zealand J Obstet Gynaecol (2003) 43:129-133.

Magann, EF, et al.: Lack of utility of amniotic fluid index in predicting perinantal morbidity and mortality. American Journal of Obstetrics and Gynecology (2001) 184(4):778-779.

Magann, EF, et al.: Low amniotic fluid volume is poorly identified in singleton and twin pregnancies using the 2×2 cm pocket technique of the biophysical profile. Southern Medical Journal (1999) 92(8):802-805.

Magann, EF, et al.: Relative amniotic fluid distribution by upper versus lower uterine quadrants reflects neither actual volume or pregnancy outcome. American Journal of Obstetrics and Gynecology (2001) 186(6 Suppl):S162.

Magann, EF, et al.: The effect of maternal intravenous hydration on amniotic fluid volume. Abstract, American Journal of Obstetrics and Gynecology (2001) 184(1):S102.

Magann, EF, et al.: Ultrasound estimate of amniotic fluid volume: color doppler overdiagnosis of oligohydramnios. Obstet Gynecol (2001) 98(1):71-74.

Magann, EF, et al.: Ultrasound estimated amniotic fluid volume by the AFI and single deepest pocket (SDP) indices: how well do they predict low, normal and high amniotic fluid volume? Abstract, American Journal of Obstetrics and Gynecology (2002) 187(6):S145.

Magann, EF, et al.: Ultrasound estimation of amniotic fluid volume using the largest vertical pocket containing umbilical cord: measure to or through the cord? Ultrasound Obstet Gynecol (2002) 20:464-467.

Mancuso, KM, et al.: Epidural analgesia for cephalic version: a randomized trial. Obstet Gynecol (2000) 95(5):648-651.

Mann, SE, et al.: Novel technique for assessing amniotic fluid volume: use of a three-dimensional bladder scanner. J Matern Fetal Med (2000) 9:308-310.

Manning, FA, et al.: Ultrasound assessment of amniotic fluid volume: distribution of largest vertical pocket measurements. Abstract, American Journal of Obstetrics and Gynecology (2000) 182(1 part 2):S109.

Manson, JM: Genomics of human fetal morphogenesis. Children's Hospital of Philadelphia. Abstract (2003).

Mazza, V, et al.: Sonographic early fetal gender assignment: a longitudinally study in pregnancies after in vitro fertilization. Ultrasound Obstet Gynecol. (2001) 17:513-516.

McKenna, D, et al.: A randomized trial using ultrasound to identify the high-risk fetus in a low-risk population. Obstetrics & Gynecology, (2003) 101(4):626-632.

Meyer, WJ, et al.: Effect of amniotic fluid volume on ultrasonic fetal weight estimation. J Ultrasound Med. (1995) 14(3):193-197.

Minagawa, K, et al.: Possible correlation between high levels of IL-18 in the cord blood of pre-term infants and neonatal development of periventricular leukomalacia and cerebral palsy. (2002) 17(3):164-170.

Mirghani, HM, et al.: The effect of maternal fasting on the fetal biophysical profile. Int J Gynaecol Obstet (2003) 81:17-21.

Morris, JM, et al.: The usefulness of ultrasound assessment of amniotic fluid in predicting adverse outcome in prolonged pregnancy: a prospective blinded observational study. BJOG: an International Journal of Obstetrics and Gynaecology, Oxford, UK (2003) 110(11)989-994.

Mueller-Navia, J, et al.: Complete and precise characterization of marker chromosomes by application of microdissection in prenatal diagnosis. Hum. Genet. (1995) 96(6):661-667.

Mussap, M, et al.: Predictive value of amniotic fluid cystatin C levels for the early identification of fetuses with obstructive uropathies. BJOG (2002) 109:778-783.

Myles, T, et al.: Normal ultrasonic evaluation of amniotic fluid in low-risk patients at term. Journal of Reproductive Medicine (2002) 47(8):621-624.

Nakai, A, et al.: Accuracy and reproducibility of ultrasound measurements in obstetric management. Gynecol. Obstet Invest (2002) 54:31-36.

Oepkes, D: Invasive versus non-invasive testing in red-cell alloimmunized pregnancies. Eur J Obstet Gynecol Reprod Biol (2000) 92:83-89.

Ohashi, G, et al.: Boundary estimation method for ultrasonic 3D imaging. Proc SPIE Int. Soc. Opt. Eng. (1993) 1898:480-486.

O'Herlihy, C, et al.: Ultrasound monitoring of amniotic fluid deepest pool in prolonged pregnancy: an alternative to routine induction of labor. Abstract, American Journal of Obstetrics and Gynecology (2001) 184(1):S10.

Olson, G, et al.: Ultrasound assessment of amniotic fluid volume for the diagnosis of oligohydramnios. Abstract, American Journal of Obstetrics and Gynecology (2001) 185(6 Suppl):S251.

Owen, P, et al.: Is there a relationship between fetal weight and amniotic fluid index? Ultrasound Obstet Gynecol (2002) 20:61-63.

Pasquini, L, et al.: Amniotic fluid analysis as a screening test in term and post-term pregnancy. Minerva Ginecol (2003) 55(1):69-75.

Perni, S, et al.: The association of amniotic fluid index with estimated fetal weight. Abstract, American Journal of Obstetrics and Gynecology (2003) 189 (6 suppl):S235.

Petres, RE, et al.: Ultrasound in the intrauterine diagnosis and treatment of fetal abnormalities. Clin. Obstet. Gynecol. (1982) 25(4):753-772.

Petrikovsky, BM, et al.: Viral studies on amniotic fluid from fetuses with and without abnormalities detected by prenatal sonography. J Reprod. Med. (2003) 48:230-232.

Piazze, J, et al.: Fetal lung maturity and fetal flowmetry changes. Acta Biomed Ateneo Parmense (2000) 71(Suppl 1):431-435.

Polivkova, Z, et al.: Prenatal cytogenetic diagnosis at the Department of Medical Genetics GENNET-Klimentsk. Ceska Gynekol (2000) 65(3):142-146.

Pautamo, J, et al.: Diagnosing fetal urinary tract abnormalities: benefits of MRI compared to ultrasonography. Acta Obstet Gynecol Scand. (2000) 79:65-71.

Rielly, MR, et al.: A theoretical and experimental investigation of nonlinear ultrasound propagation through tissue mimicking fluids. IEEE Ultrasonics Symposium. (2000) 2:1355-1358.

Rielly, MR: A theoretical and experimental investigation of nonlinear propagation of ultrasound through tissue mimicking media. University of Bath (UK), European Abstracts, (2001) 62-04C:600.

Rodgers, L, et al.: Acute circulatory and respiratory collapse in obstetrical patients: a case report and review of the literature. AANA J (2000) 68(5):444-450.

Ross, MG: Amniotic fluid volume determination. Am J Obstet Gynecol (1993) 169(2, Pt. 1):435-437.

Ross, MG: Maternal dehydration-fetal/amniotic fluid homeostasis. Harbor-UCLA Research & Educ Inst. Abstract (2002).

Sagiv, C, et al.: Application of semiautomatic boundary detection algorithm for the assessment of amniotic fluid quantity from ultrasound images. Ultrasound in Medicine and Biology (1999) 25(4):515-526.

Sahin, B, et al.: Estimation of the amniotic fluid volume using the cavalieri method on ultrasound images. Int J Gynaecol Obstet (2003) 82:25-30.

Sapin, E, et al.: Transabdominal amnioinfusion to avoid fetal demise and intestinal damage in fetuses with gastroschisis and severe oligohydramnios. J Pediatr Surg. (2000) 35:598-600.

Schaefer-Graf, UM, et al.: Amniotic fluid insulin levels and fetal abdominal circumference at time of amniocentesis in pregnancies with diabetes. Diabet Med. (2003) 20:349-354.

Schrimmer, DB, et al.: Sonographic evaluation of amniotic fluid volume. Clin Obstet Gynecol (2002) 45(4):1026-1038.

Seffah, JD, et al.: Aminotic fluid index for screening late pregnancies. East African Medical Journal (1999) 76(6):348-351.

Sherer, DM: A review of amniotic fluid dynamics and the enigma of isolated oligohydramnios. American Journal of Perinatology (2002) 19(5):253-266.

Shulman, A, et al.: Prenatal identification of esophageal atresia: the role of ultrasonography for evaluation of functional anatomy. Prenat. Diagn. (2002) 22:669-674.

Siddiqi, TA, et al.: In situ human obstetrical ultrasound exposimetry: estimates of derating factors for each of three different tissue models. Ultrasound Med. Biol. (1995) 21(3):379-391.

Silver, RK, et al.: A reappraisal of amniotic fluid alpha-fetoprotein measurement at the time of genetic amniocentesis and midtrimester ultrasonography. J Ultrasound Med (2001) 20:631-637.

Silver, RK, et al.: Clinical implications of atypical chromosome abnormalities diagnosed prenatally. Obstet Gynecol (1999) 94(6):925-928.

Sim, DAJ: Ultrasonographic observations on human pregnancy. Queeen's U of Belfast (Northern Ireland), Doc. No. AAIC284473, European Abstracts (1991) 54/02:527.

Strauss, A, et al.: Prenatal diagnosis of renal dysplasia. Z Geburtshilfe Neonatol (2001) 205:71-75.

Thilaganathan, B, et al.: Effectiveness of prenatal chromosomal analysis using multicolor fluorescent in situ hybridisation. BJOG (2000) 107(2):262-266.

Thomenius, KE: Impact of nonlinear propagation on temperature distributions caused by diagnostic ultrasound. IEEE Ultrasonics Symposium Proceedings. (1998) 2:1409-1413.

Tongsong, T, et al.: The rapid biophysical profile for assessment of fetal well-being. J Obstet Gynaecol Res (1999) 25(6):431-436.

Tsatsaris, V., et al.: Prenatal diagnosis of bilateral isolated fetal hyperechogenic kidneys. Is it possible to predict long term outcome? BJOG (2002) 109:1388-1393.

Ulmer, R, et al.: Diagnosis of aneuploidy by fluorescence in situ hybridization (FISH); its value in pregnancies at risk for chromosomal aberrations. Z Geburtshilfe Neonatol (2002) 204:1-7.

Vidigal, PV, et al.: Prenatal toxoplasmosis diagnosis from amniotic fluid by PCR. Rev Soc Bras Med Trop (2002) 35(1):1-6.

Vishnoi, G, et al.: Photon migration through fetal head in utero using continuous wave, near-infrared spectroscopy: development and evaluation of experimental and numerical models. Journal of Biomedical Optics. (2000) 5(2):163-172.

Volio, I, et al.: Cytogenetical prenatal diagnosis by amniocentesis during the II and III gestation trimesters in Costa Rica. Rev Biol Trop, Abstract (2001) 49(3-4):1227-1236.

Wang, CJ, et al.: Three-dimensional ultrasonic images of normal fetus. Chang Gung Med. J (2001) 24(8):476-482.

Warner, J: A comparison of fetal behavior in hypertensive and normotensive pregnant women. ISBN-0-612-65653-5, Thesis, Queen's University, Kingston, Ontario, Canada (2001) 1-96.

Warren, RC, et al.: First trimester diagnosis of hypophosphatasia with a monoclonal antibody to the liver/bone/kidney isoenzyme of alkaline phosphatase. Lancet. (1985) 2(8460):856-858.

Weissman, A, et al.: Sonographic measurement of amniotic fluid volume in the first trimester of pregnancy. J Ultrasound Med (1996) 15(11):771-774.

Wilson, RD, et al.: Fetal ultrasound abnormalities: correlation with fetal karyotype, autopsy findings, and postnatal outcome-five-year prospective study. Am. J. Med. Genet. (1992) 44(5):586-590.

Yin, L, et al.: Placental morphometriological study on prolonged and delayed pregnancy and its relationship to pregnancy outcome. Chinese J Obstet Gynecol (1998) 33(7):415-418.

Zauhar, G, et al.: Studies of acoustic streaming in amniotic fluid and water. Proceedings of the International Fed of Med and Biological Engineering (2001) 2:596-599.

Zhang, X, et al.: Prenatal gene diagnosis of alpha-thalassemias. Chinese J Obstet Gynecol (1998) 33(3):139-141.

Zlatnik, MG, et al.: Amniotic fluid index measured with the aid of color flow doppler. J Matern Fetal Neonatal Med (2003) 13:242-245.

Zlatnik, MG, et al.: Using color-flow doppler to aid in the measurement of amniotic fluid index overestimates oligohydramnios. American Journal of Obstetrics and Gynecology (2000) 182(1 part 2):S147.

Agnew, C.L., et al., "Maternal/fetal dehydration: prolonged effects and response to oral rehydration," Am. J. Physiol., 1993, vol. 264: pp. R197-R203.

Albuquerque, C.A., et al., "Human and Ovine Amniotic Fluid Composition Differences: Implications for Fluid Dynamics," The Journal of Maternal-Fetal Medicine, 1990, vol. 8: pp. 123-129.

Cardin, Jr., J.P., et al., "Fetal and Maternal Response to Intravenous Infusion of a Thromboxane Synthetase Inhibitor," American Journal of Obstetrics and Gynecology, Oct. 1990, vol. 163, No. 4: pp. 1345-1349.

Curran, M.A., et al., "Human amniotic fluid mathematical model: Determination and effect of intramembranous sodium flux," American Journal of Obstetrics and Gynecology, 1998, vol. 178: pp. 484-490.

Desai, M., et al., "Maternal DDAVP-induced hyponatremia preserves fetal urine flow during acute fetal hemorrhage," Am. J. Physiol. Regul. Integr. Comp. Physiol., Apr. 10, 2003, vol. 285: pp. R373-R379.

Dodd, A., et al., "Dehydration increases the renal response to atrial natriurectic peptide in fetal sheep," American Journal of Obstetrics and Gynecologgy, Dec. 1992, vol. 167, No. 6: pp. 1710-1716.

Ervin, M.G., et al., "Arginine Vasotocin in Ovine Fetal Blood, Urine and Amniotic Fluid," J. Clin. Invest., May 1985, vol. 75: pp. 1696-1701.

Ervin, M.G., et al., "Changes in Steady State Plasma Arginine Vasotocin Levels Affect Ovine Fetal Renal and Cardiovascular Function," Endocrinology, 1986, vol. 118, No. 2: pp. 759-765.

Ervin, M.G., et al., "Fetal recirculation of amniotic fluid arginine vasopressin," Am. J. Physiol., 1986, vol. 250: pp. E253-E258.

Ervin, M.G., et al., "Regulation of Fetal Atrial Natriuretic Factor and Arginine Vasopressin Secretion," Prrogress in Endocrinology, 1998: pp. 685-690.

Ervin, M.G., et al., "Renal effects of ovine fetal arginine vasopressin secretion in response to maternal hypersmolality," American Journal of Obstetrics and Gynecology, 1986, vol. 155, No. 6: pp 1341-1347.

Ervin, M.G., et al., "Vascular effects alter early-gestation fetal renal responses to vasopression," Am. J. Physiol., 1994, vol. 266: pp. R722-R729.

Kullama, L.K., et al., "Intraamniotic deamino(D-Arg8)-vasopressin: Prolonged effects on ovine fetal urine flow and swallowing," American Journal of Obstetrics and Gynecology, 1996, vol. 174: pp. 78-84.

Kullama, L.K., et al., "Ovine fetal swallowing and renal responses to oligohydramnios," Am. J. Physiol., 1994, vol. 266: pp. R972-R978.

Kullama, L.K., et al., "Ovine maternal and fetal renal vasopressin receptor response to maternal dehydration," American Journal of Obstetrics and Gynecology, Dec. 1992, vol. 167, No. 6: pp. 1717-1722.

Leake, R.D., et al., "Diurnal Variations in Plasma Arginine Vasotocin (AVT) Concentrations in the Ovine Fetus," Life Sciences, 1986, vol. 38: pp. 1485-1490.

Leake, R.D., et al., "Fetal Arginine Vasopressin under Basal and Hypoosmolal Conditions," Biology of the Neonate, 1987, vol. 51: pp. 204-211.

Leake, R.D., et al., "Ovine Fetal-Maternal Water Transfer is Independent of Fetal Prolactin Levels," Pediatric Research, 1985, vol. 19, No. 10: pp. 986-988.

Maan, S.E., et al., "Mathematic modeling of human amniotic fluid dynamics," American Journal of Obstetrics and Gynecology, 1996, vol. 175: pp. 937-944.

Mann, S.E., et al., "Ovine fetal adaptations to chronically reduced urine flow: preservation of amniotic fluid volume," J. Appl. Physiol., 1996, vol. 81, No. 6: pp. 2588-2594.

Nijland, M.J., et al., "DDAVP-induced maternal hyposmolality increases ovine fetal urine flow," Am. J. Physiol., 1995, vol. 268: pp. R358-R365.

Ogundipe, O.A., et al., "Assessments of Fetal Swallowed Volume: Tracer Disappearance Versus Esophageal Flow," J. Soc. Gynecol. Invest., 1994, vol. 1, No. 1: pp. 37-44.

Ogundipe, O.A., et al., "Prophylactic Amnioinfusion for Oligohydramnios: A Reevaluation," Obstetrics and Gynecology, Oct. 1994, vol. 84, No. 4, Part 1: 7 pp.

Roberts, T.J., et al., "Maternal 1-deamino-8-D-arginine-vasopressin-induced sequential decreases in plasma sodium concentration: Ovine fetal renal responses," American Journal of Obstetrics and Gynecology, 1999, vol. 180: pp. 82-90.

Ross, M.G., et al., "1-Deamino-[8-D-arginine] vasopressin-induced maternal plasma hypoosmolality increases ovine amniotic fluid volume," American Journal of Obstetrics and Gynecology, 1996, vol. 174: pp. 1118-1125.

Ross, M.G.,e t al., "Amniotic fluid ionic concentration in response to chronic fetal vasopression infusion," Am. J. Physiol., 1985, vol. 249: pp. E287-E291.

Ross, M.G., et al., "Artifactually Elevated Basal Uterine Tonus Resulting from Measurement of Hydrostatic Pressure by Transducer-Tipped Intrauterine Catheters," Journal of Perinatology, 1994, vol. XIV, No. 5: pp. 408-410.

Ross, M.G., et al., "Bulk Flow of Amniotic Fluid Water in Response to Maternal Osmotic Challenge," American Journal of Obstetrics and Gynecology, Nov. 15, 1983, vol. 147, No. 6: pp. 691-701.

Ross, M.G., et al., "Central angiotensin II stimulation of ovine fetal swallowing," J. Appl. Physiol., 1994, vol. 76, No. 3: pp. 1340-1345.

Ross, M.G., et al., "Continuous ovine fetal hemorrhage: sensitivity of plasma and urine arginine vasopressin response," Am. J. Physiol., 1986, vol. 251: pp. E464-E469.

Ross, M.G., et al., "Correlation of maternal plasma volume and composition with amniotic fluid index in normal human pregnancy," The Journal of Maternal-Fetal and Neonatal Medicine, 2004, vol. 15 pp. 104-108.

Ross, M.G., et al., "Fetal and maternal plasma atrial natriuretic factor response to angiotensin II infusion," Dec. 1991, vol. 165, No. 6: pp. 1635-1641.

Ross, M.G., et al., "Fetal Atrial Natriuretic Factor and Arginine Vasopressin Responses to Hyperosmolality and Hypervolemia," Pediatric Research, 1988, vol. 24, No. 3: pp. 318-321.

Ross, M.G., et al., "Fetal Lung Fluid Response to Maternal Hyperosmolality," Pediatric Pulmonology, Jan.-Feb. 1986, vol. 2, No. 1: pp. 40-43.

Ross, M.G., et al., "Fetal Rehydration Via Intraamniotic Fluid: Contribution of Fetal Swallowing," Pediatric Research, 1991, vol. 29, No. 2: pp. 214-217.

Ross, M.G., et al., "Fetal Swallowing: Relation to Amniotic Fluid Regulation," Clinical Obstetrics & Gynecology, Jun. 1997, vol. 47, No. 2: pp. 352-365.

Ross, M.G., et al., "Intraruminal rehydration of ovine fetuses," Am. J. Physiol., 1991, vol. 261: pp. R1381-R1387.

Ross, M.G., et al., "Isovolemic hypotension in ovine fetus: plasma arginine vasopressin response and urinary effcts," Am. J. Physiol., 1986, vol. 250: pp. E564-E569.

Ross, M.G., et al., "Maternal dehydration-rehydration: fetal plasma and urinary responses," Am. J. Physiol., 1988, vol. 255: pp. E674-E679.

Ross, M.G., et al., "Ovine fetal swallowing response to intracerebroventricular hypertonic saline," J. Appl. Physiol., 1995, vol. 78, No. 6: pp. 2267-2271.

Ross, M.G., et al., "Ovine Fetal Urine Contribution to Amniotic and Allantoic Compartments," Biology of the Neonate, 1988, vol. 53: pp. 98-104.

Ross, M.G., et al., "Plasma Atrial Natriuretic Peptide Response to Volume Expansion in the Ovine Fetus," American Journal of Obstetrics and Gynecology, 1987, vol. 157, No. 5: pp. 1292-1297.

Sherman, D.J., et al., "Ovine fetal lung fluid response to intravenous saline solution infusion: Fetal atrial natriuretic factor effect," American Journal of Obstetrics and Gynecology, 1988, vol. 159: pp. 1347-1352.

Spong, C.Y., et al., "Amniotic fluid index predicts the relief of variable decelerations after amnioinfusion bolus," American Journal of Obstetrics and Gynecology, 1996, vol. 175: pp. 1066-1070.

Spong, C.Y., et al., "Prophylactic amnioinfusion for meconium-stained amniotic fluid," American Journal of Obstetrics and Gynecology, 1994, vol. 171: pp. 931-935.

Umur, A., et al., "Amniotic fluid and hemodynamic model in monochorionic twin pregnancies and twin-twin transfusion syndrome," Am. J. Physiol. Regulatory Integrative Comp. Physiol., 2001, vol. 280: pp. R1499-R1509.

Umur, A., et al., "Discordant Fetal Growth Patterns in Monochorionic Twin Pregnancies Described by Simple Algebraic Relations," Fetal Diagn. Ther., 2003, vol. 18: pp. 301-308.

Umur, A., et al., "Does amniotic fluid volume affect fetofetal transfusion in monochorionic twin pregnancies? Modelling two possible mechanisms," Phys. Med. Biol., 2002, vol. 47: pp. 2165-2177.

Umur, A., et al., "Fetal urine and amniotic fluid in monochorionic twins with twin-twin transfusion syndrome: Simulations of therapy," American Journal of Obstetrics and Gynecology, 2001, vol. 185: pp. 996-1003.

Umur, A., et al., "Monochorionic Twins and Twin-Twin Transfusion Syndrome: The Protective Role of Arterio-arterial Anastomoses," Placenta, 2002, vol. 23: pp. 201-209.

Van Den Wijngaard, J.P.H.M., et al., "Modeling a hydropic recipient twin in twin-twin transfusion syndrome," Am. J. Physiol. Regul. Integr. Comp. Physiol., 2005, vol. 288: pp. R799-R814.

Van Den Wijngaard, J.P.H.M., et al., "Simulation of therapy in a model of a nonhydropic and hydropic recipient in twin-twin transfusion syndrone," American Journal of Obstetrics and Gynecology, 2005, vol. 193: pp. 1972-1980.

Van Gemert, M.J.C., et al., "Twin-twin transfusion syndrome: etiology, severity and rational management," Curr. Opin. Obstet. Gynecol., 2001, vol. 13: pp. 193-206.

Grover, J. et al., "Three-Dimensional Method for Determination of Amniotic Fluid Volume in Intrauterine Pockets," Obstetrics & Gynecology, vol. 90, No. 6, Dec. 1997, pp. 1007-1010.

* cited by examiner

METHOD AND SYSTEM FOR MEASURING AMNIOTIC FLUID VOLUME AND/OR ASSESSING FETAL WEIGHT

CROSS REFERENCE TO RELATED APPLICATION

This application claims the benefit of the earlier filing date of U.S. Provisional Patent Application No. 60/467,983, filed May 5, 2003 and incorporated herein by reference.

BACKGROUND

1. Field

Method and system for measuring amniotic fluid volume.

2. Background

Amniotic fluid is the fluid within the pregnant uterus enclosed by the fetal membranes and placenta. Amniotic fluid helps protect and cushion the fetus and plays a role in the development of various fetal organs including the lungs, kidneys, and gastrointestinal tract. Too much or too little amniotic fluid may be associated with abnormalities in development of the fetus or other pregnant complications.

Currently, ultrasound techniques are used to provide a measurement of amniotic fluid volume referred to as the amniotic fluid index (AFI). AFI may be assigned by adding linear determinations of amniotic fluid pocket depths and/or two-dimensional assessments of amniotic fluid pocket dimensions. AFI data obtained may be compared to data listing normal values for the pregnancy stage of the patient for which an AFI is determined. AFI may provide a way to screen for certain abnormalities during pregnancy. However, AFI is not a good predictor of actual amount of amniotic fluid.

Accurate assessment of amniotic fluid volume may be important for various reasons. First, it provides an indication of fetal stress. Fetal stress may cause the amniotic fluid volume to decrease due to fetal renal metabolic changes and decreased urine output, which constitutes the main generator of amniotic fluid. Second, low amniotic fluid volume renders the fetus at risk for compression of the umbilical cord, which is often an emergency situation. Accordingly, an accurate assessment of amniotic fluid volume may be useful in screening for certain fetal stress conditions and/or other pregnant complications.

BRIEF DESCRIPTION OF THE DRAWINGS

Embodiments may best be understood by referring to the following description and accompanying drawings, in which.

DETAILED DESCRIPTION

In the following description, specific details are set forth. However, it is understood that embodiments may be practiced without these specific details. In other instances, well-known circuits, components, software programs, structures and techniques have not been shown in detail to avoid obscuring the understanding of this description.

Figure 1:
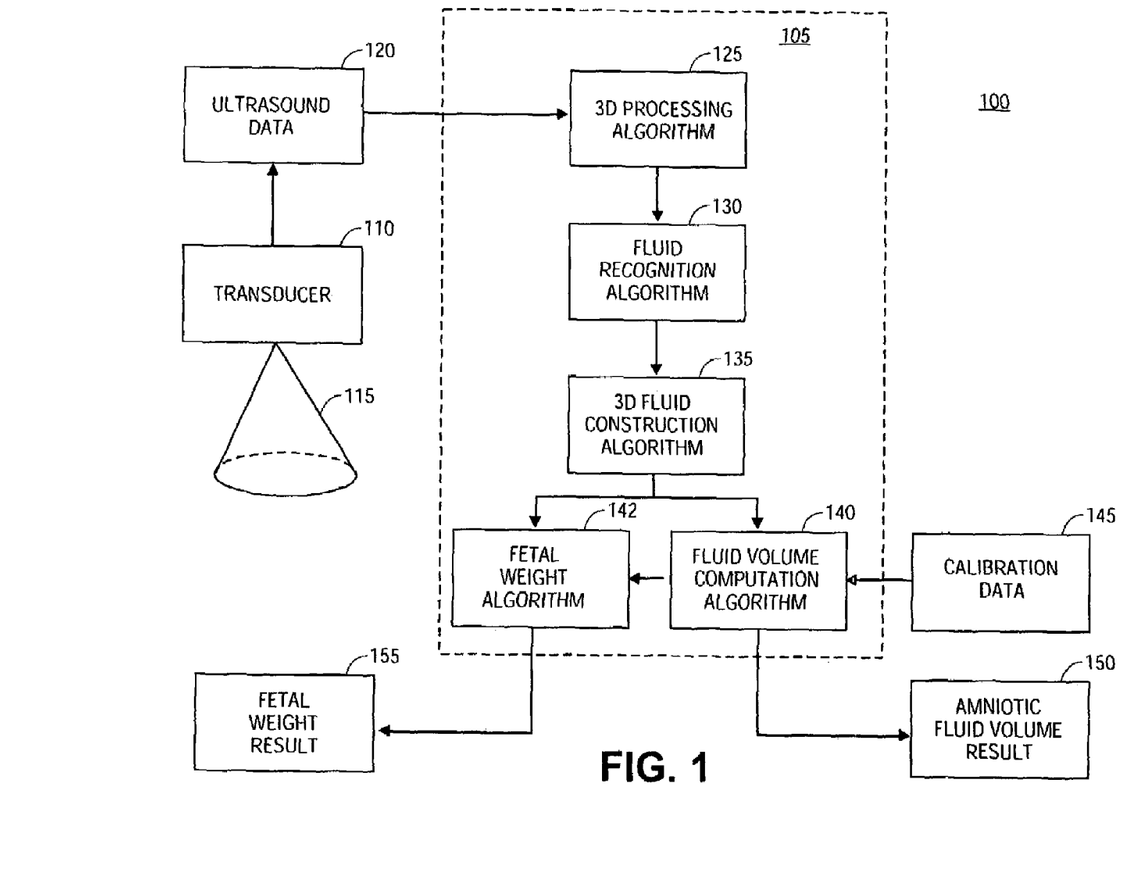
FIG. 1 is a block diagram of an ultrasound system for measuring amniotic fluid volume according to one embodiment.

FIG. 1 depicts a block diagram of ultrasound system 100 for measuring amniotic fluid volume and/or assessing fetal weight according to one embodiment. System 100 includes an ultrasound apparatus to generate data representative of a three-dimensional construction of a pregnant uterus being scanned. In one embodiment, the ultrasound apparatus includes a handheld unit for use external to the patient. In one embodiment, the ultrasound apparatus includes a scanhead with transducer 110 that is moved within the scanhead to perform three-dimensional scanning.

It should be understood that system 100 may be implemented with many different ultrasound configurations for scanning a three-dimensional region within a patient being scanned. For example, system 100 may be implemented with an array of transducer elements which moves an ultrasound beam vertically and/or horizontally across a three-dimensional region by a manual or mechanical operation.

During the scanning process, transducer 110 transmits ultrasound energy into a region of a patient being scanned and receives reflected ultrasound energy, or echoes, from various structures within the patient's body, including uterus wall, various parts of the fetus, amniotic fluid, placenta, umbilical cord, etc. For example, by appropriately delaying the pulses applied to each transducer element, a focused ultrasound beam may be transmitted along a desired scan line. Reflected ultrasound energy from a given point within a body of a patient is received by the transducer elements at different points in time. Transducer 110 may convert the received ultrasound energy to a scanner signal that represents the reflected energy level along a given scan line. The process may be repeated for multiple scan lines to generate two-dimensional slices (also referred to as "scan planes") of the target region of the body of the patient. The scan planes may have a conical shape 115, wherein scan lines originate at the center of the transducer and are directed at different angles. A linear, curvilinear or any other scan pattern can also be utilized.

Ultrasound data 120 of a uterus acquired by scanning an abdomen of a pregnant women are collected in a memory for subsequent processing. Ultrasound data 120 generated by transducer 110 may be in the form of a series of data representing multiple scan planes of the scanned uterus. In accordance with one embodiment, ultrasound data 120 generated by transducer 110 is processed by amniotic fluid volume computation (AFVC) application 105. AFVC application 105 may be executed within a processing element of the ultrasound apparatus. Alternatively, AFVC application 105 can be executed within a processing unit external to the ultrasound apparatus. Representatively, ultrasound data 120 may be generated in an examination room of a medical office or a hospital. That data may be transmitted directly from the examination room via, for example, Internet, wired communications network, or wireless communication network to AFVC application 105 located outside the examination room and, in another embodiment, outside the medical office or hospital. According to this embodiment, data regarding amniotic fluid volume may be received at a location remote to the patient. This allows someone, other than a treating physician or specialist to generate ultrasound data 120. In another embodiment, ultrasound data 120 and/or an amniotic fluid volume result may be stored in a memory associated with ultrasound system 100 (memory located locally and/or remotely) for later evaluation or manipulation. For example, such data may be used to develop statistics regarding amniotic fluid volume based on an age, race or health history of a patient. Alternatively, the data may be used in teaching exercises to train physicians.

In one embodiment, amniotic fluid volume computation (AFVC) application 105 includes 3D (three-dimensional) processing algorithm 125, fluid differentiating algorithm 130, 3D fluid construction algorithm 135 and fluid volume computation algorithm 140. First, 3D processing algorithm 125 processes ultrasound data 120 by performing, among other things, operations necessary for organizing two-dimensional scan planes of data. For example, 3D processing algorithm 125 may be configured to align the two-dimensional scan planes of data to generate three-dimensional representation of the scanned region. In one embodiment, the three-dimensional representation may include data representing tissues (e.g., uterus wall and fetus parts) and fluid (e.g., amniotic fluid) contained within a pregnant uterus.

The data generated by 3D processing algorithm 125 is passed to fluid recognition algorithm 130, which processes the data to differentiate data representing fluid from data representing tissues (e.g., fetus, uterine wall, etc.). Once fluid recognition algorithm 130 has differentiated fluid from tissues, 3D fluid construction algorithm 135 is used to provide data representing a three-dimensional construction of fluid distributed within pregnant uterus. The data generated by 3D fluid construction algorithm 135 is passed to fluid volume computation algorithm 140 to quantify amniotic fluid volume based on the three-dimensional representation of fluid contained within the uterus. Alternatively, in another implementation, amniotic fluid volume may be computed without generating a three-dimensional representation of fluid contained within the uterus. For example, in this implementation, amniotic fluid volume may be computed based on the number of ultrasound data (e.g., pixel data) representing amniotic fluid. In one embodiment, amniotic fluid volume result 150 computed by AFVC application 105 is provided to a user (e.g., physician) in actual fluid volume measurement, for example, in centiliters (cl), etc.

In another embodiment, the data generated by 3D processing algorithm 130 may be used to assess fetal weight. For example, fluid recognition algorithm 130 may, in one embodiment, differentiate not only fetal and maternal tissue from amniotic fluid, but also fetal tissue from maternal tissue. In this manner, a volume of fetal tissue may be determined from which an assessment of fetal weight may be determined (e.g., through fetal weight algorithm 142). Fetal weight result 155 is provided to user as a weight measurement, for example, in grams or pounds.

To improve the accuracy of volume measurement of amniotic fluid contained within a uterus or weight of fetal tissue, in one embodiment, calibration data 145 may be used to calibrate the amniotic fluid volume or fetal tissue weight computed by algorithm 140. Calibration data 145 may include information with regard to the position of the transducer relative to the scanned uterus. For example, the actual distance between the transducer and the scanned uterus may be used to calibrate the computed amniotic fluid volume or fetal tissue weight.

In one embodiment, ultrasound system 100 is used solely for the purpose of assessment of amniotic fluid volume and/or assessing fetal weight. Accordingly, AFVC application 105 is configured to provide amniotic fluid volume result 150 (and/or a fetal weight assessment) without providing a three-dimensional image of the fetal anatomy. When the determination of the amniotic fluid volume and/or fetal weight is the only objective, providing amniotic fluid volume and/or fetal weight measurement without visualization of the fetal anatomy enables physicians to focus solely on the evaluation of the amniotic fluid volume or fetal weight without having to assess other conditions of the fetus that may be visible on three-dimensional images generated by the ultrasound data.

In another embodiment, ultrasound system 100 provides a three-dimensional image of the uterus being scanned in a limited number of colors and/or gray scale values. For example, ultrasound system 100 may utilize one-bit pixel values, which uses two colors or two gray scale values to differentiate fluid and tissue of a scanned uterus; one color may be assigned to represent fluid and another color may be assigned to represent tissues. By doing so, it may be difficult or impossible to discern certain features or to differentiate between certain tissue types. Accordingly, the only information that may be learned from the scan is the volume and distribution of the amniotic fluid within the pregnant uterus and/or the fetal weight.

Figure 2:
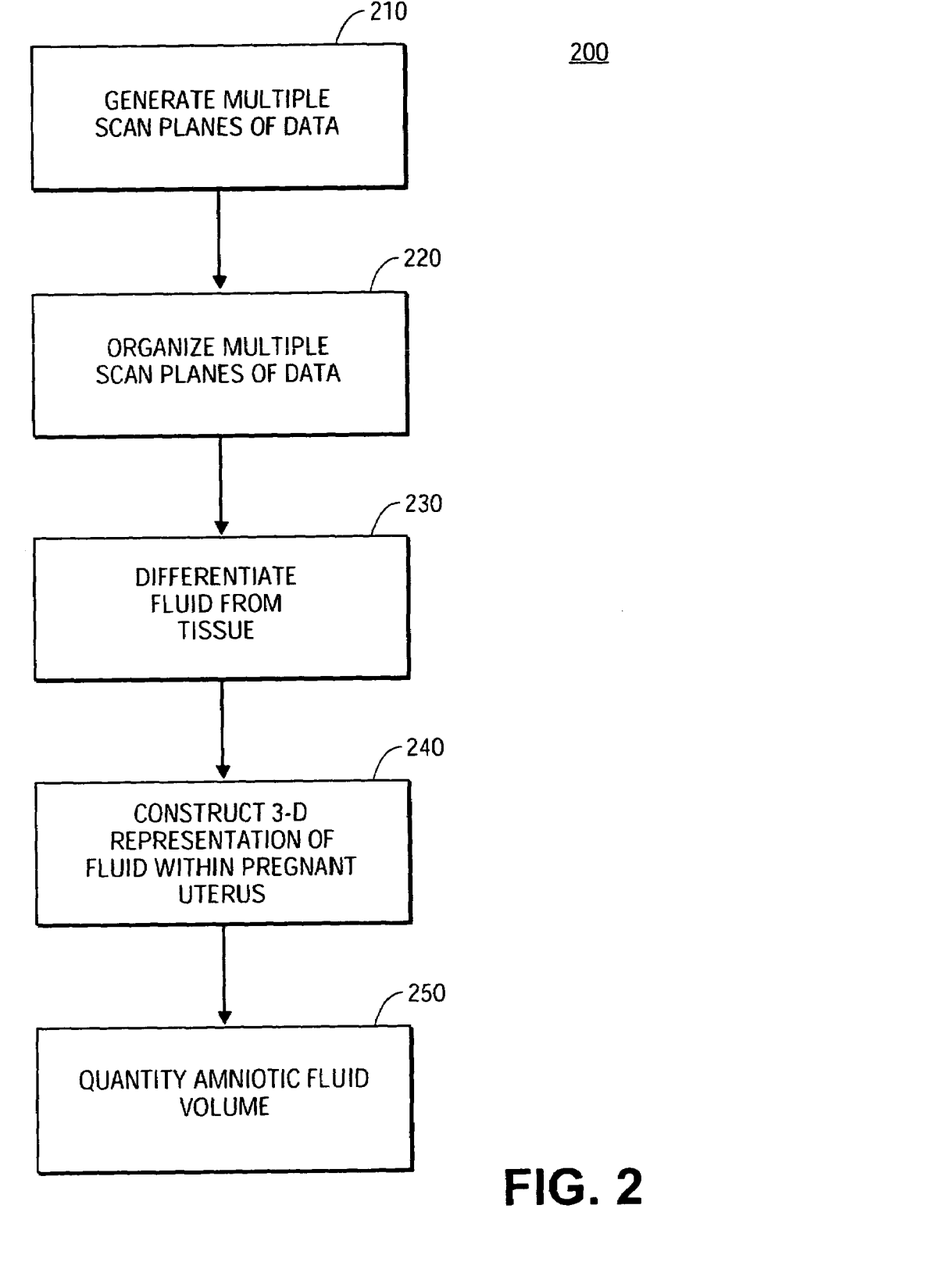
FIG. 2 is a flowchart of operations of computing amniotic fluid volume according to one embodiment.

FIG. 2 depicts a flowchart of operations of computing amniotic fluid volume according to one embodiment. In functional block 210, an ultrasound apparatus is used to generate a series of data representing two-dimensional slices ("scan planes") of the uterus being scanned. Because there is amniotic fluid surrounding the fetus, including above and below the fetus, multiple scan planes should include data representing all or substantially all of fluid surrounding the fetus. Once a scanning process has been completed, the two-dimensional scan planes are organized to render a three-dimensional representation of the scanned uterus in block 220. This may be accomplished by aligning the scan planes of data to form a three-dimensional representation of the scanned region.

In functional block 230, the three-dimensional representation of the scanned uterus is examined to differentiate fluid from tissue (e.g., fetal parts, umbilical cord, uterine walls and placenta) and, optionally, fetal tissue from maternal tissue. In one implementation, this is accomplished by classifying each ultrasound data, as a fluid or tissue (including soft tissue and bone) in order to differentiate tissues forming the uterus wall and fetus parts from the amniotic fluid distributed between the fetus and the uterus wall. In another implementation, amniotic fluid is differentiated from tissue by detecting outer surfaces of the fetus and inner surfaces of the uterine wall and identifying the amniotic fluid distributed therebetween.

Once data representing fluid has been differentiated from data representing tissue, three-dimensional representation of fluid contained within the scanned uterus may be constructed in block 240. With the ability to differentiate fluid from other surrounding tissues within a uterus (e.g., fetal tissue) and to generate three-dimensional representation of fluid, the user may, for example, be able to view the three-dimensional representation of the fluid to examine the distribution of the amniotic fluid within the pregnant uterus.

In functional block 250, the three-dimensional representation of fluid contained within the scanned uterus is used to compute an actual amount of amniotic fluid contained within the scanned uterus. There may be a small amount of fluid in the fetus (e.g., fluid in bladder and stomach). In one implementation of amniotic fluid volume computation, the volume of fluid detected within the fetus is not accounted for in determining the amniotic fluid volume in order to obtain an accurate measurement of amniotic fluid. In another implementation, amniotic fluid volume computation involves quantifying the volume of fluid within the fetus in utero and subtracting such fluid volume from the total amount of fluid detected within the uterus.

In another embodiment, the amniotic fluid volume is computed by quantifying an interior volume of the scanned uterine volume and subtracting the volume of space occupied by the fetus in utero and other tissues within the scanned uterus, such as umbilical code and placenta. In yet another embodiment, amniotic fluid volume is computed without generating a three-dimensional representation of fluid contained within the uterus. In this embodiment, amniotic fluid volume is computed based on the number of ultrasound data (e.g., pixel data) representing amniotic fluid.

Figure 3A:
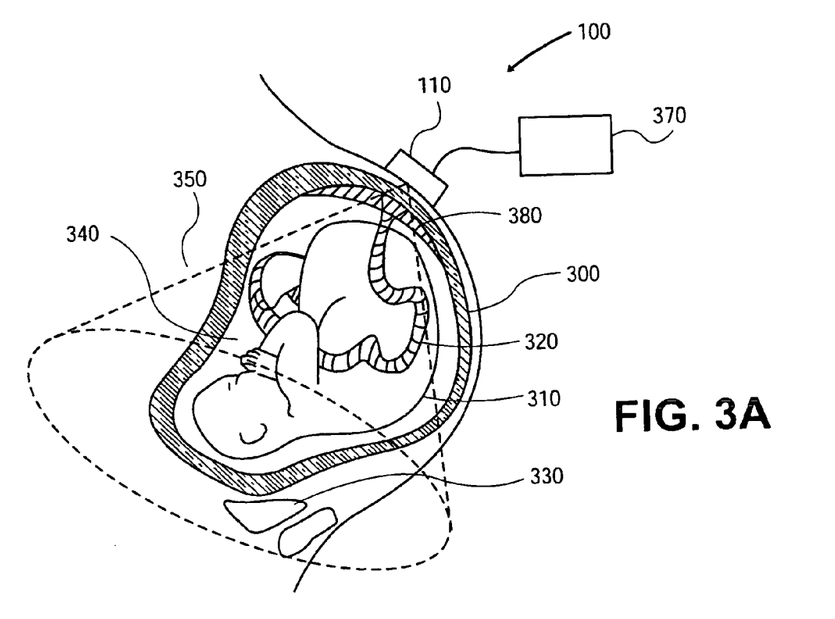
FIG. 3A is a simplified representation of the ultrasound system being used to scan a pregnant uterus.

In operation, transducer 110 of ultrasound apparatus 370 may be placed at the uterine fundus and scanned in the direction of the feet of a patient, as shown in FIG. 3A. During scanning process, transducer 110 is used to transmit ultrasound energy into the abdomen region of a patient and receives reflected ultrasound energy from various parts of the body of the patient, including uterus wall 300, various parts of the fetus 310, amniotic fluid 340, placenta 380, umbilical cord 320, etc. For example, by appropriately delaying the pulses applied to each transducer element, a focused ultrasound beam may be transmitted along a desired scan line. Reflected ultrasound energy from a given point within the body of the patient is received by the transducer elements at different points in time. Transducer 110 may convert the received ultrasound energy to a scanner signal that represents the reflected energy level along a given scan line. The process may be repeated by moving transducer elements in a pattern (e.g., arc) to generate multiple scan planes of data of the scanned uterus. Each scan plane may represent a two-dimensional slice, wherein scan lines originate at the center of the transducer and are directed at different angles. Once ultrasound apparatus 370 has completed its scanning process, AFVC application may be used to process the multiple planes of the data to compute an amount of amniotic fluid contained within the uterus.

In one example, the transducer is operated at a frequency such that generated waves travel through amniotic fluid without echoing or with a determined echo response frequency. Fetal tissue and maternal tissue (e.g., umbilical cord, placenta and uterine walls) each produce an echo response frequency different than the response frequency of amniotic fluid, if any. The fetal tissue and maternal tissue are classified, for example, in a memory, in one embodiment, based on a minimum response frequency value that is greater than a response frequency of the amniotic fluid. To determine an amount of amniotic fluid present in the uterus, the volume of the uterus or a scanned sector is defined based on scanned data. The fetal tissue volume and maternal tissue volume within the uterus is then determined by collecting the classified fetal tissue and maternal tissue and calculating a volume of the classified fetal tissue based on scanned data. The volume of the classified fetal tissue and maternal tissue is then subtracted from the volume of the uterus to obtain a sum equivalent to amniotic fluid volume. Alternatively, a software algorithm may be utilized to discriminate the borders of ultrasound frequency responses consistent with fluid, from responses consistent with that of maternal or fetal tissue. An analysis of the determined volume will yield amniotic fluid volume in a scanned sector. In either example, an assessment of fetal weight may also be made by determining a volume of fetal tissue (separate from maternal tissue) and calculating a fetal weight based on the fetal volume determination, for example, by multiplying the fetal volume by a density attributed to the fetal tissue.

Figure 3B:
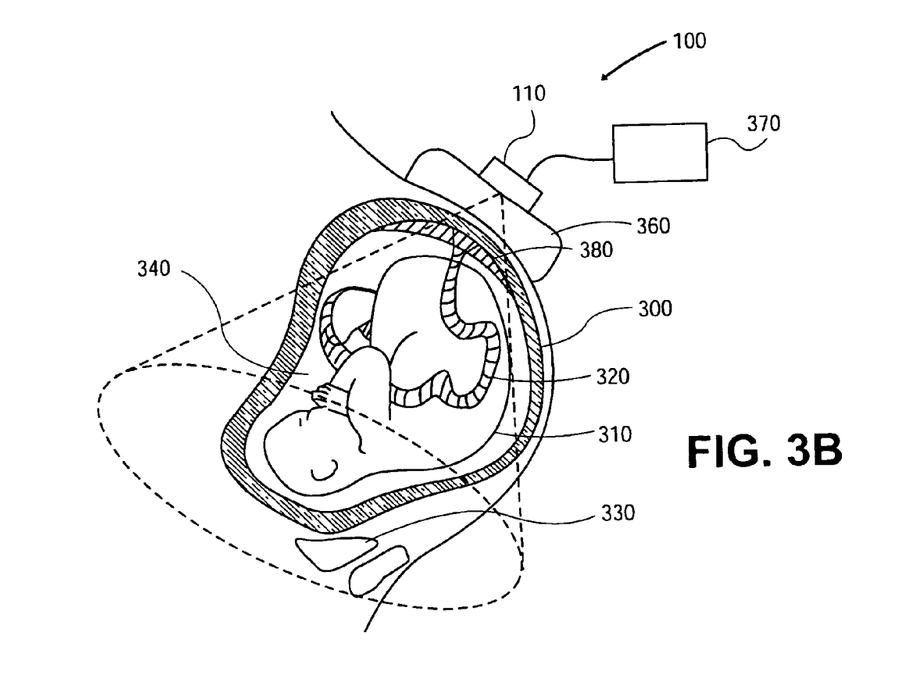
FIG. 3B is a simplified representation of a pillow, such as a pillow of water or gel pad, placed between a transducer and an abdomen of a pregnant woman.

It should be noted that a relatively wide scan angle is generally required to scan a substantial portion of a pregnant uterus from one transducer location since the length of a term uterus may be upwards of 35 to 40 cm. In one embodiment, a pillow, such as a pillow of water or gel pad 360, is placed between transducer and an abdomen of a pregnant woman, as shown in FIG. 3B, in order to achieve a wider scan of the pregnant uterus.

In one embodiment, ultrasound apparatus 370 is capable of scanning a full term uterus that is about 35-40 cm in size, from a single scanning location (e.g., uterine fundus). Additionally, in one embodiment, ultrasound apparatus 370 is capable of generating and receiving ultrasound signals that are reflected from the uterus walls above the fetus as well as below the fetus.

In another embodiment, ultrasound apparatus 370 is used to scan different regions or sectors of the uterus (e.g., four quadrants of the uterus) from a number of different scanning locations. And, data representing different regions of the uterus are combined to construct a three-dimensional representation of the entire uterus. Any suitable method may be utilized to combined data representing different scanned regions. Once a three-dimensional representation of the entire uterus has been completed, the fluid volume computation application may used to quantify the amount of amniotic fluid volume based on the combined data representing the entire uterus.

While several embodiments are described, those skilled in the art will recognize that the spirit and scope of the claims are not limited to the embodiments described, but can be practiced with modification and alteration. The description is thus to be regarded as illustrative instead of limiting.

What is claimed is:

1. An apparatus comprising:
   a memory to store multiple ultrasound scan planes of data of a scanned pregnant uterus; and
   a processor coupled to the memory to generate a three-dimensional construction of the entire scanned uterus based on the multiple scan planes of data and being configured to compute a volume of amniotic fluid contained within an entirety of the scanned uterus based on the three-dimensional construction of the uterus, wherein the computation includes subtraction of a value obtained from the three-dimensional construction of the uterus.

2. The apparatus of claim 1, wherein the processor is configured to differentiate data representing fluid from data representing tissues and to generate a three-dimensional construction of fluid contained within the scanned uterus based on the differentiated data.

3. The apparatus of claim 2, wherein the amniotic fluid volume is computed based on data representing the three-dimensional construction of fluid contained within the scanned uterus.

4. The apparatus of claim 1, wherein the processor is configured to combine different sets of data representing different regions of the uterus to form a three-dimensional construction the entire scanned uterus.

5. The apparatus of claim 1, wherein a volume of amniotic fluid contained within an entirety of the scanned uterus ignores any amniotic fluid within a fetus in the uterus.

6. A method comprising:
   scanning a pregnant uterus with ultrasound;
   generating data representing a three-dimensional construction of the scanned uterus; and
   computing a volume of amniotic fluid in an entirety of the uterus based on the three-dimensional construction of the uterus, wherein the computation includes subtraction of a value obtained from the three-dimensional construction of the uterus.

7. The method of claim 6, wherein the amniotic fluid volume is computed based on data representing a three-dimensional construction of fluid contained within the scanned uterus.

8. The method of claim 7, wherein the three-dimensional construction of fluid contained with the scanned uterus is generated by differentiating data representing fluid from data representing tissues.

9. The method of claim 6, further comprising providing an observable image of amniotic fluid distribution within the scanned uterus without providing an image of fetal anatomy.

10. The method of claim 6, wherein the amniotic fluid volume is computed by quantifying an interior volume of the scanned uterine volume and subtracting a volume of space occupied by a fetus in utero, umbilical cord and placenta.

11. The method of claim 6, wherein the data representative of three-dimensional construction of the scanned uterus is generated by combining different sets of data representing different regions of the uterus.

12. The method of claim 6, wherein the data representative of three-dimensional construction of a pregnant uterus is generated by placing an ultrasound transmission medium between a transducer and a pregnant woman's abdomen.

13. The method of claim 6, wherein the amniotic fluid volume computation includes subtracting an amount of fluid detected within fetus in utero from a total amount of fluid detected within the scanned uterus.

14. The method of claim 6, wherein computing a volume of amniotic fluid contained within an entirety of the scanned uterus ignores any amniotic fluid within a fetus in the uterus.

15. The method of claim 6, further comprising providing a result of a volume of amniotic fluid within the uterus without providing an image of fetal anatomy.

16. A system comprising:
   an ultrasound apparatus to scan a pregnant uterus and to generate data representative of a three-dimensional construction of the scanned uterus; and
   a processor configured to compute a volume of amniotic fluid contained within an entirety of the scanned uterus based on the three-dimensional construction of the entire uterus, wherein the computation includes subtraction of a value obtained from the three-dimensional construction of the uterus.

17. The system of claim 16, wherein the amniotic fluid volume is computed based on data representing a three-dimensional construction of fluid contained within the scanned uterus.

18. The system of claim 17, wherein the three-dimensional construction of fluid contained with the scanned uterus is generated by differentiating data representing fluid from data representing tissues.

19. The system of claim 16, wherein the data representative of three-dimensional construction of the scanned uterus is generated by combining different sets of data representing different regions of the uterus.

20. The system of claim 16, wherein the system is configured to provide an observable image of amniotic fluid distribution within the scanned uterus without providing an image of fetal anatomy.

21. The system of claim 16, wherein the amniotic fluid volume is computed by quantifying an interior volume of the scanned uterine volume and subtracting a volume of space occupied by a fetus in utero, umbilical cord and placenta.

22. The system of claim 16, wherein the data representative of three-dimensional construction of a pregnant uterus is generated by placing an ultrasound transmission medium between a transducer and an abdomen of a pregnant woman.

23. The system of claim 16, wherein a calibration data is used to calibrate the amniotic fluid volume computed by the processor.

24. The system of claim 16, wherein the amniotic fluid volume is computed by subtracting an amount of fluid detected within fetus in utero from a total amount of fluid detected within the scanned uterus.

25. The system of claim 16, wherein a volume of amniotic fluid contained within an entirety of the scanned uterus ignores any amniotic fluid within a fetus in the uterus.

26. The system of claim 16, wherein the system is configured to provide a result of a volume of amniotic fluid contained within the entirety of scanned uterus and not to provide an image of fetal anatomy.

* * * * *

UNITED STATES PATENT AND TRADEMARK OFFICE
CERTIFICATE OF CORRECTION

PATENT NO.        : 7,399,278 B1
APPLICATION NO.   : 10/836963
DATED             : July 15, 2008
INVENTOR(S)       : Michael G. Ross It is certified that error appears in the above-identified patent and that said Letters Patent is hereby corrected as shown below:

On Page 4, under Other Publications, correct the 17th reference in the first column; delete "Pautamo" and insert -- Poutamo --.

On Page 5, under Other Publications, correct the 21st reference in the first column; delete "Maan" and insert -- Mann --.

Signed and Sealed this
Ninth Day of August, 2011

David J. Kappos
*Director of the United States Patent and Trademark Office*